US012121641B2

(12) United States Patent
Plahey

(10) Patent No.: US 12,121,641 B2
(45) Date of Patent: Oct. 22, 2024

(54) DIALYSIS MACHINE WITH INTELLIGENT LOAD MONITORING

(71) Applicant: Fresenius Medical Care Holdings, Inc., Waltham, MA (US)

(72) Inventor: Kulwinder Plahey, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 967 days.

(21) Appl. No.: 17/022,428

(22) Filed: Sep. 16, 2020

(65) Prior Publication Data

US 2022/0080091 A1   Mar. 17, 2022

(51) Int. Cl.
*A61M 1/26* (2006.01)
*A61M 1/14* (2006.01)
*A61M 1/28* (2006.01)

(52) U.S. Cl.
CPC .......... *A61M 1/267* (2014.02); *A61M 1/1524* (2022.05); *A61M 1/154* (2022.05); *A61M 1/155* (2022.05); *A61M 1/159* (2022.05); *A61M 1/262* (2014.02); *A61M 1/28* (2013.01); *A61M 1/1522* (2022.05); *A61M 1/1565* (2022.05); *A61M 2205/12* (2013.01); *A61M 2205/14* (2013.01); *A61M 2205/15* (2013.01); *A61M 2205/3306* (2013.01); *A61M 2205/3317* (2013.01)

(58) Field of Classification Search
None
See application file for complete search history.

(56) References Cited

U.S. PATENT DOCUMENTS

| 4,033,379 | A | 7/1977 | Tooley |
| 2003/0217962 | A1 | 11/2003 | Childers et al. |

(Continued)

FOREIGN PATENT DOCUMENTS

| CO | 7010798 A2 | 7/2014 |
| JP | 2006181386 A | 7/2006 |

(Continued)

OTHER PUBLICATIONS

International Search Report and Written Opinion for the International Patent Application No. PCT/US2021/044452, mailed Jan. 20, 2022, 20 pages.

*Primary Examiner* — Jonathan M Peo
(74) *Attorney, Agent, or Firm* — KDW Firm PLLC

(57) ABSTRACT

Dialysis systems and methods for operating dialysis machines (e.g., peritoneal dialysis machines) for conducting dialysis treatments are disclosed. The dialysis system may include a dialysis machine for transferring dialysate to a patient from a dialysate source. The dialysate may flow from the dialysate source through a cartridge or cassette (e.g., a disposable cartridge or cassette) positionable within the dialysis machine. The dialysis machine includes a piston or pump for pumping fluid (e.g., dialysate) from the cassette to the patient. In various embodiments, the dialysis machine includes one or more sensors for monitoring a condition. For example, the dialysis machine may include sensor(s) for monitoring proper alignment of the cassette within the cassette compartment, or sensors mounted on the pump head for monitoring a leak during a dialysis operation, or sensors for monitoring improper operation of the pumps (e.g., pistons), or a combination thereof.

25 Claims, 8 Drawing Sheets

(56) References Cited

U.S. PATENT DOCUMENTS

| | | | |
|---|---|---|---|
| 2003/0217964 A1* | 11/2003 | Eu | A61M 1/28 |
| | | | 210/500.1 |
| 2003/0220598 A1 | 11/2003 | Busby et al. | |
| 2004/0019313 A1 | 1/2004 | Childers et al. | |
| 2007/0125709 A1 | 6/2007 | Nigam | |
| 2009/0009290 A1 | 1/2009 | Kneip et al. | |
| 2010/0312174 A1* | 12/2010 | Hoffman | A61M 1/155 |
| | | | 604/29 |
| 2011/0106003 A1* | 5/2011 | Childers | A61M 1/154 |
| | | | 604/29 |
| 2014/0319035 A1 | 10/2014 | Burbank et al. | |
| 2015/0025449 A1 | 1/2015 | Yuds et al. | |
| 2015/0314058 A1* | 11/2015 | O'Mahony | F04B 49/002 |
| | | | 417/63 |
| 2017/0080140 A1* | 3/2017 | Lauer | A61M 1/36226 |
| 2019/0351123 A1* | 11/2019 | Norman | A61M 1/1696 |
| 2019/0358381 A1* | 11/2019 | Westenbrink | F04B 51/00 |

FOREIGN PATENT DOCUMENTS

| | | | | |
|---|---|---|---|---|
| WO | 2019094927 A1 | 5/2019 | | |
| WO | WO-2019087096 A1 * | 5/2019 | | A61M 1/16 |

\* cited by examiner

DIALYSIS MACHINE WITH INTELLIGENT LOAD MONITORING

FIELD OF THE DISCLOSURE

The disclosure generally relates to dialysis machines, and more particularly to a dialysis machine including one or more sensors to detect (i) proper loading, inserting, positioning, alignment, etc. of a cassette within the dialysis machine, (ii) fluid or leakage on a face of a pump, (iii) proper operation of the pumps, and (iv) a combination thereof.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated PD machines, called PD cyclers, are designed to control the entire PD process so that it can be performed at home, usually overnight, without clinical staff in attendance.

A dialysis machine, such as a PD machine, may include one or more containers (e.g., bags) containing a fluid (e.g., a dialysate) for patient infusion. In addition, a PD machine may include a removable and/or replaceable cartridge or cassette (used interchangeably without the intent to limit) attached to one or more fluid lines for pumping fluid to and from a patient. In PD machines, for example, one or more fluid lines are inserted into an abdomen of a patient for flowing fresh dialysate and removing used dialysate, waste, and excess fluid. As the cassette facilitates pumping of the fluid, the dialysis machine may monitor fluid delivery, fluid temperature, flow path, and pressure.

The cassette may be insertable into the PD machine and enclosed within the PD machine during a dialysis operation. At the conclusion of the operation, the cassette may be removed and properly disposed of. The cassette and accompanying fluid flow lines, valves, and/or connectors may be single use items.

In use, the PD machines and cassette include an interface where a pump, a piston, a pump assembly, a piston assembly, etc. (terms used interchangeably herein without the intent to limit) of the PD machine contacts the cassette. That is, the cassette typically includes a membrane such as, for example, a rigid material that forms one or more channels, pump chambers, etc. in the cassette. The rigid material may be bonded to a flexible membrane that can be distorted by the pump of the PD machine. The fluid (e.g., dialysate) may be contained between the rigid material and the flexible membrane. In use, the fluid (e.g., dialysate) may be moved from the PD machine to the patient via the action of a piston or pump head in the PD machine on the membrane of the cassette.

In some cases, a patient or caregiver may insert the cassette into the PD machine in such a way that the interface between the cassette and the pump isn't properly aligned causing misalignment between the pump chambers formed in the cassette and the pistons, pump head, valve actuators, etc. of the PD machine. Misalignment of the cassette within the PD machine may cause leaks in the cassette when the pump heads contact the cassette outside of the intended target area of the cassette.

In addition, and/or alternatively, during manufacturing of the dialysis machines, problems may arise such as, for example, using parts that are bent, etc. that may cause the pump heads to be misaligned in the dialysis machine. As a result, engagement of the pump heads in the dialysis machine with the pump chamber of the cassette positioned within the dialysis machine may be inaccurate, which may cause problems resulting in leaks in the cassette or prevent proper positioning, alignment, etc. of the pump heads with the pump chambers of the cassette.

Cassette leaking may affect the quality of the fluid flow and the exchange of the dialysate with the patient, potentially affecting a patient's treatment procedure (e.g., dialysate may not be delivered to the patient's peritoneal cavity or incorrect amounts of fluid may be delivered or removed from the patient's peritoneal cavity). In addition, when leaks develop and remain undetected in the PD machine, leaking fluid may damage the PD machine, possibly beyond repair, requiring full replacement. This can be problematic when a patient requires frequent dialysis treatment and needs to obtain an immediate replacement, which can be costly.

A leak developed at the interface between the piston or pump head of the pump in the PD machine and the membrane proximate the pump chamber of the cassette can be particularly problematic since the pump chamber contains one of the largest volume of fluid collection in the cassette and, therefore, a leak at this location can lead to large amounts of leaking fluid. As such, it would be advantageous to detect a leak right at, or adjacent to, the interface between the piston or pump head and the membrane of the cassette. In addition, and/or alternatively, it would be advantageous to monitor the pumps (e.g., piston, pump heads, etc.) to confirm proper operation.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment is disclosed. The dialysis system comprises a dialysis machine for transferring dialysate to a patient from a dialysate source, the dialysis machine including a housing including a cassette compartment, a pump positioned within the housing, and one or more sensors and a cassette positionable within the cassette compartment, the cassette being in fluid communication with the patient and the dialysate source; wherein, when the cassette is positioned within the cassette compartment, movement of the pump causes dialysate to be transferred from the dialysate source to the patient and wherein the one or more sensors are arranged and configured to detect proper alignment of the cassette within the cassette compartment.

In this and other embodiments, the one or more sensors is one or more limit switches, the one or more limit switches arranged and configured so that proper alignment of the cassette within the cassette compartment causes the cassette to trigger the one or more limit switches.

In this and other embodiments, the dialysis machine includes one or more locating pins extending from a surface thereof, the one or more limit switches built into the locating pins.

In this and other embodiments, the one or more sensors includes an optical sensor arranged and configured to detect a location of the cassette within the cassette compartment.

In this and other embodiments, the optical sensor is arranged and configured to detect a location of a perimeter of the cassette relative to the cassette compartment to detect proper alignment of the cassette within the cassette compartment.

In this and other embodiments, the cassette includes one or more registration marks printed on an outer surface thereof, the one or more sensors includes an image sensor arranged and configured to detect alignment of the cassette relative to the cassette compartment based on imaging of the one or more registration marks on the cassette.

In this and other embodiments, the one or more sensors includes one or more capacitive sensors arranged and configured to detect proper alignment of the cassette within the cassette compartment.

In this and other embodiments, the one or more capacitive sensors are arranged and configured to detect if the cassette is properly seated within the cassette compartment via determining if the cassette is positioned adjacent with a surface of the cassette compartment.

In this and other embodiments, the dialysis system further comprises one or more capacitive sensors positioned on a head of the pump, the one or more capacitive sensors arranged and configured to detect a presence of a liquid on the head of the pump or on a surface of the cassette.

In this and other embodiments, the dialysis system further comprises one or more sensors arranged and configured to detect proper axial extension of the pump.

In this and other embodiments, the one or more sensors arranged and configured to detect proper axial extension of the pump includes a plurality of proximity sensors positioned about the pump.

In this and other embodiments, the plurality of proximity sensors are arranged and configured to detect alignment of the pump during extension.

In this and other embodiments, the one or more sensors are configured to send a signal based on a detection of improper alignment of the cassette within the cassette compartment; wherein the signal is sent to a user interface of the dialysis machine, an audible indicator, or a light indicator, or a combination thereof.

In this and other embodiments, the dialysis machine is arranged and configured to automatically terminate the transfer of dialysate to the patient from the dialysate source upon receipt of the signal.

According to an exemplary embodiment of the present disclosure, a dialysis system for conducting a dialysis treatment is disclosed. The dialysis system comprises a dialysis machine for transferring dialysate to a patient from a dialysate source, the dialysis machine including a housing including a cassette compartment, a pump positioned within the housing, and one or more sensors, and a cassette positionable within the cassette compartment, the cassette being in fluid communication with the patient and the dialysate source, wherein, when the cassette is positioned within the cassette compartment, movement of the pump causes dialysate to be transferred from the dialysate source to the patient and wherein the one or more sensors are arranged and configured to: (i) detect proper alignment of the cassette within the cassette compartment, (ii) detect a leak within the dialysis machine, (iii) detect proper axial alignment of the pump; or (iv) a combination thereof.

In this and other embodiments, the one or more sensors is one or more limit switches, the one or more limit switches arranged and configured so that proper alignment of the cassette within the cassette compartment causes the cassette to trigger the one or more limit switches.

In this and other embodiments, the dialysis machine includes one or more locating pins extending from a surface thereof, the one or more limit switches built into the locating pins.

In this and other embodiments, the one or more sensors includes an optical sensor arranged and configured to detect a location of the cassette within the cassette compartment.

In this and other embodiments, the optical sensor is arranged and configured to detect a location of a perimeter of the cassette relative to the cassette compartment to detect proper alignment of the cassette within the cassette compartment.

In this and other embodiments, the cassette includes one or more registration marks printed on an outer surface thereof, the one or more sensors includes an image sensor arranged and configured to detect alignment of the cassette relative to the cassette compartment based on imaging of the one or more registration marks on the cassette.

In this and other embodiments, the one or more sensors includes one or more capacitive sensors arranged and configured to detect proper alignment of the cassette within the cassette compartment.

In this and other embodiments, the one or more capacitive sensors are arranged and configured to detect if the cassette is properly seated within the cassette compartment via determining if the cassette is positioned adjacent with a surface of the cassette compartment.

In this and other embodiments, the dialysis system further comprises one or more capacitive sensors positioned on a head of the pump, the one or more capacitive sensors arranged and configured to detect a presence of a liquid on the head of the pump or on a surface of the cassette.

In this and other embodiments, the dialysis system further comprises one or more sensors arranged and configured to detect proper axial extension of the pump.

In this and other embodiments, the one or more sensors arranged and configured to detect proper axial extension of the pump includes a plurality of proximity sensors positioned about the pump.

In this and other embodiments, the plurality of proximity sensors are arranged and configured to detect alignment of the pump during extension.

In this and other embodiments, the one or more sensors are configured to send a signal based on a detection of improper alignment of the cassette within the cassette compartment; wherein the signal is sent to a user interface of the dialysis machine, an audible indicator, or a light indicator, or a combination thereof.

In this and other embodiments, the dialysis machine is arranged and configured to automatically terminate the transfer of dialysate to the patient from the dialysate source upon receipt of the signal.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
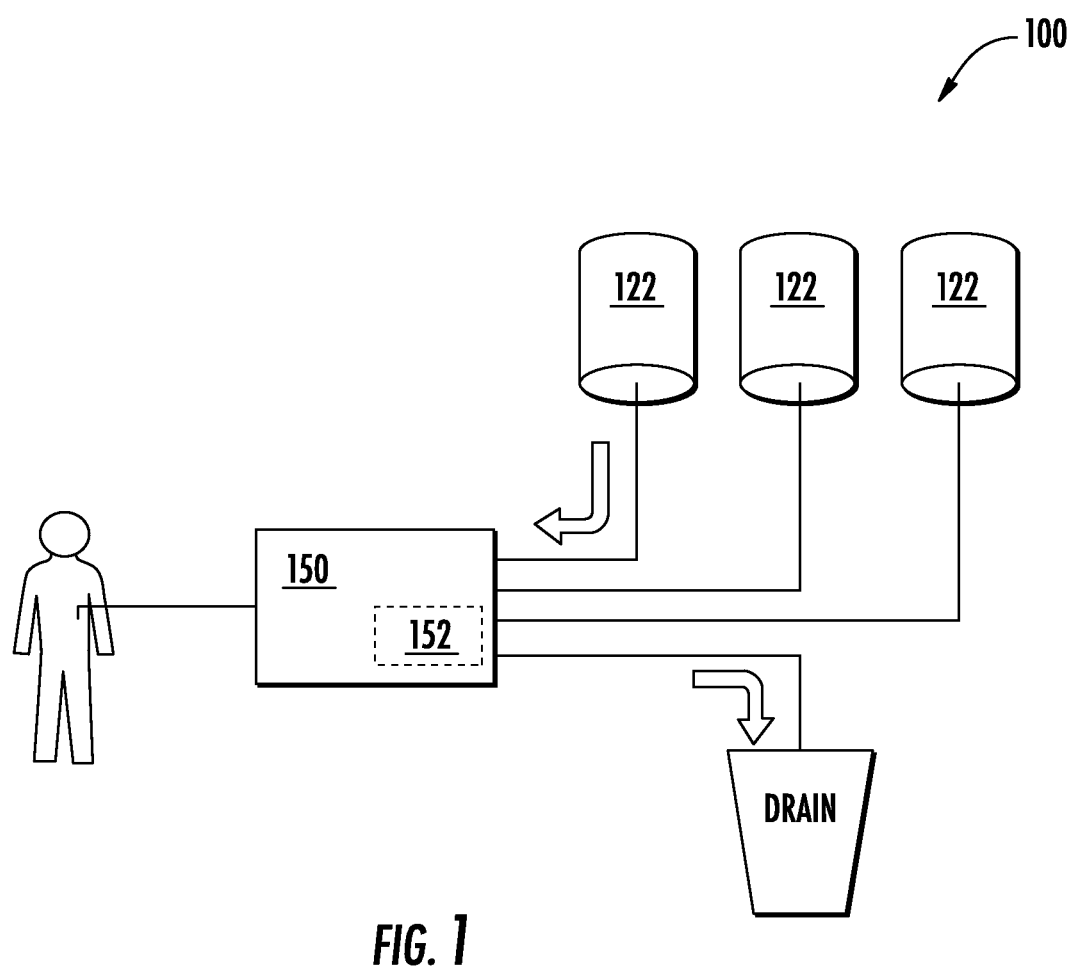
FIG. 1 illustrates an example of an embodiment of a dialysis system.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of systems and methods arranged and configured to detect proper loading, inserting, positioning, alignment, etc. (terms used interchangeably herein without the intent to limit) of the cassette into a dialysis machine, and/or fluid or leakage at the interface between the pumps and the cassette, and/or proper operation of the pumps (e.g., piston, pump heads, etc.) of the dialysis machine will now be described. It will be appreciated that dialysis operation is often not able to be monitored manually on a continual basis for leaks or other conditions, or it may not be efficient or practical to do so. This is particularly the case where dialysis is performed while a patient is sleeping, e.g., in the case of PD machines that are often self-administered in the home of a patient. Automatic detection and shutdown is therefore important to prevent any potential machine malfunction or delivery of improper treatment.

In accordance with one or more aspects of the present disclosure, a dialysis machine such as, for example, a PD machine, may be able to quickly detect misalignment of the cassette within the PD machine, any leaks at the interface between the cassette and the pumps, and/or mis-operation of the pumps (e.g., piston, pump heads, etc.) that may develop. For example, it would be beneficial for a dialysis machine to quickly detect misalignment of a cassette within the PD machine. In addition, and/or alternatively, it would be beneficial for a dialysis machine to quickly detect any leaks between the PD machine and the cassette positioned within the PD machine, and/or to detect improper operation of the pumps in the PD machine, so that operation of the dialysis machine may be shut down, thereby ensuring patient safety and limiting or eliminating the potential for damage or further damage to components of the machine. In one example of an embodiment, the PD machine may include one or more sensors to detect proper positioning of the cassette within a cassette compartment of the PD machine. In addition, and/or alternatively, in one example of an embodiment, the cassette interface between the dialysis machine and the cassette may include one or more sensors to detect a leak. In addition, and/or alternatively, in one embodiment, a pump (e.g., a piston, a pump head, etc.) positioned in a dialysis machine may include one or more sensors such as, for example, one or more capacitive sensors, disposed on a front surface of the pump (e.g., a piston, a pump head, etc.). The sensors being arranged and configured to detect fluid on the surface of the piston or pump head, or on the surface of the cassette. In addition, and/or alternatively, in one embodiment, one or more sensors can be positioned about the pump to detect proper operation (e.g., extension and retraction) of the pump (e.g., pistons).

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are hung near the PD machine 150 which may improve air content management as any air content is disposed by gravity to a top portion of the dialysate bag 122. Valves may be attached to a bottom portion of the dialysate bags 122 so fluid is drawn out and air content delivery is minimized. In one embodiment, as shown, dialysate from the dialysate bags 122 may be transferred directly to the patient through a warmer pouch, a heating chamber, or the like 152 (used interchangeably without the intent to limit) formed in the dialysis machine 150. When the dialysate has reached a predetermined temperature (e.g., approximately 98°-100° F., 37° C.) in the heating chamber 152, the dialysate may be flowed into the patient. As will be described and illustrated in greater detail below, the dialysate bags 122 may be connected to a cartridge or cassette (used interchangeably without the intent to limit), which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected to the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD machine from a dialysate concentrate, see, e.g., U.S. Pat. No. 10,076,599 to Eyrard et al., entitled "Dry Peritoneal Dialysis Concentrate System," which is incorporated by reference herein in its entirety.

Figure 2:
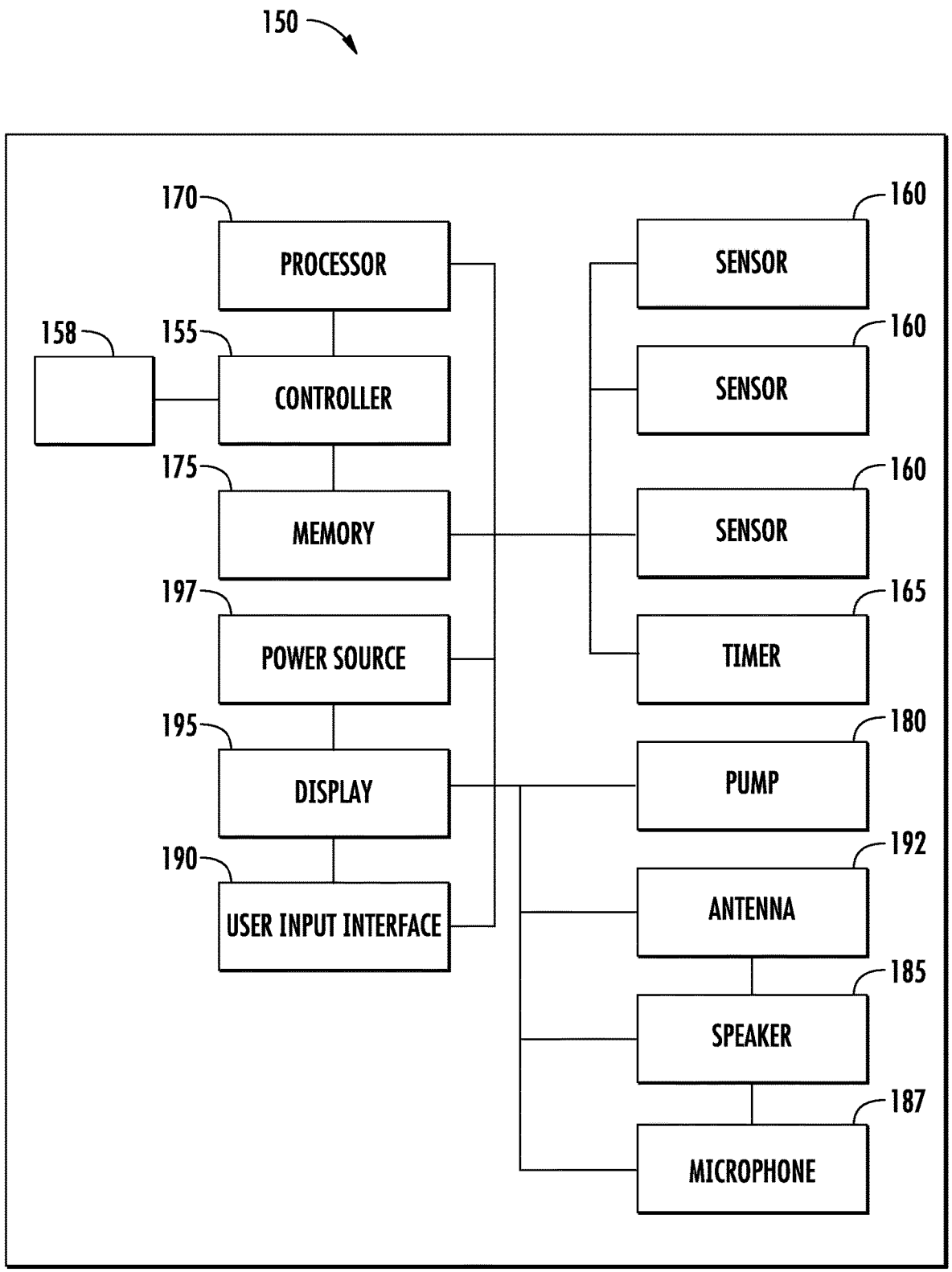
FIG. 2 is a block diagram illustrating an example of an embodiment of a dialysis machine that can be used in the dialysis system of FIG. 1.

Referring to FIG. 2, a schematic of an exemplary embodiment of a dialysis machine such as, for example, dialysis machine 150 is shown. The dialysis machine 150 may be a home dialysis machine, e.g., a PD machine, for performing a dialysis treatment on a patient, and may be included in the system 100 described above with respect to FIG. 1. In use, the dialysis machine 150 may include a controller 155 disposed in the dialysis machine 150. Alternatively, the dialysis machine 150 may be coupled to the controller 155, or other external systems, via a communication port or wireless communication links. The controller 155 may automatically control execution of a treatment function during a course of dialysis treatment.

The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing the triggering of the sensors 160. The controller 155 may communicate control signals or triggering voltages to the components of the dialysis machine 150, and may include wireless communication interfaces. The controller 155 may detect remote devices to determine if any remote sensors are available to augment any sensor data being used to evaluate the patient. For example, remote devices may include smart phone microphones, video cameras, cameras, thermal imaging cameras, in bed sensors, sleep manager applications and sensors, web cameras, fitness sensors, stand-alone sensors, and the like.

In some embodiments, the machine 150 may also include a processor 170, a memory 175, and/or the controller 155, or combinations thereof and/or the machine 150 may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, as will be described in greater detail below, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the heating chamber 152.

The dialysis machine 150 may also include a user input interface 190, which may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The dialysis machine 150 may also include a display 195 and a power source 197.

In some embodiment, the user interface 190 and display 195 may be, for example, a touch screen and a control panel operable by a user (e.g., a caregiver or a patient) to allow, for example, set up, initiation, and/or termination of a dialysis treatment. The touch screen and the control panel may allow an operator to input various treatment parameters to the dialysis machine and to otherwise control the dialysis machine. In addition, the touch screen may serve as the display. The touch screen may function to provide information to the patient and/or the operator of the dialysis system. For example, the touch screen may display information related to a dialysis treatment to be applied to the patient, including information related to a prescription. The touch screen and/or display may include one or more buttons for selecting and/or entering user information.

The dialysis machine 150 may also be connectable for remote communication. For example, the dialysis machine 150 may be configured to connect to a network. The connection to network may be via a wired and/or wireless connection. In one embodiment, the dialysis machine 150 includes, for example, an antenna or other connection component 192 to facilitate connection to a network. The antenna 192 may be, for example, a transceiver for wireless connections and/or other signal processor for processing signals transmitted and received. Other medical devices (e.g., other dialysis machines) or components may be configured to connect to the network and communicate with the dialysis machine 150.

The dialysis machine 150 may also include a speaker 185 and a microphone 187. The controller 155 being operatively connected to the speaker 185 and the microphone 187.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

In one embodiment, the processor 170 is arranged and configured to communicate with the user interface (e.g., touch screen and control panel). The processor 170 may be configured to receive data from the user interface 190 (e.g., touch screen, control panel), sensors such as, for example, weight, air content, flow, temperature, and/or pressure sensors, and control the dialysis machine 150 based on the received data. For example, the processor 170 may adjust the operating parameters of the dialysis machine 150. According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the dialysis machine 150 or may be coupled to the dialysis machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
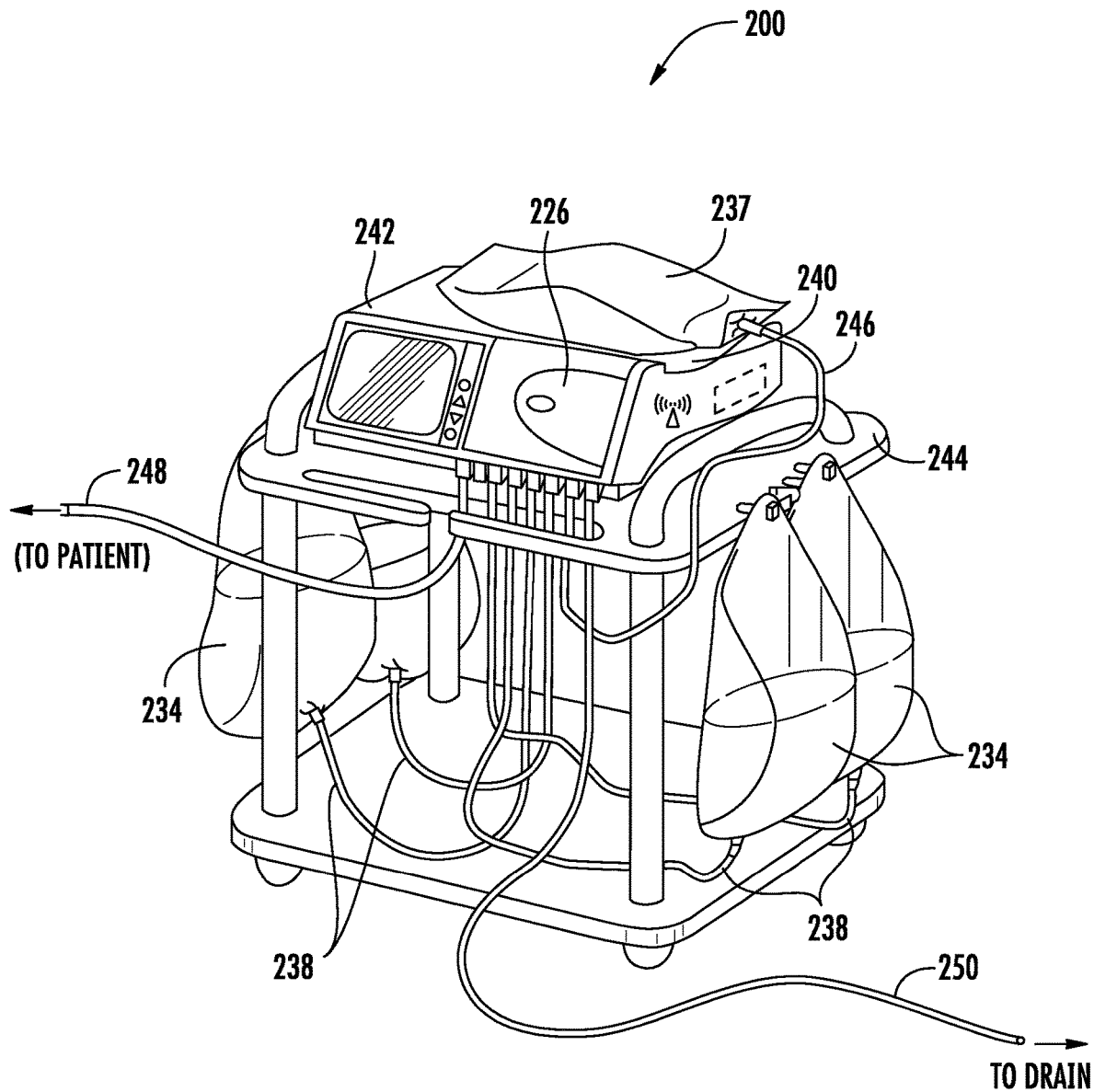
FIGS. 3A and 3B illustrate an example of an embodiment of a dialysis machine that can be used in the dialysis system of FIG. 1.
Figure 3B:
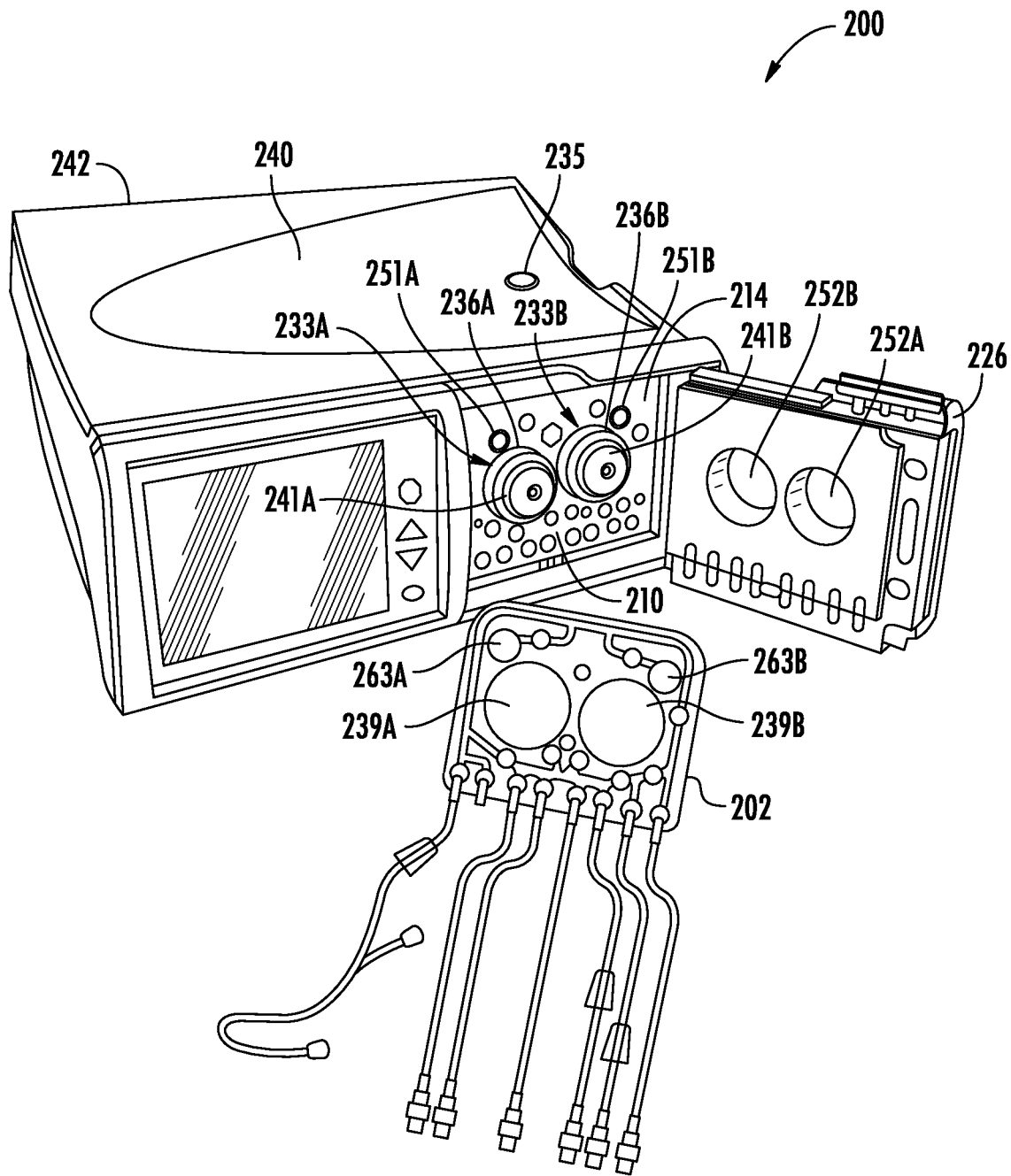

Referring now to FIGS. 3A and 3B, an example of an embodiment of a dialysis machine 200 in accordance with the present disclosure is shown. The dialysis machine 200 may include the components described above with respect to the schematic of the system 100 and the machine 150 illustrated in FIGS. 1 and 2. The machine 200 may be configured to provide home dialysis treatment, for example, PD. In some implementations, the dialysis system and machine may be a home PD system, e.g., a PD system configured for use at a patient's home.

The dialysis machine 200 may include a housing 242, a door 226, and a cassette interface including pumps for contacting a cartridge or cassette 202 (used interchangeably without the intent to limit), where the cassette 202 is located within a cassette compartment 214 formed between the cassette interface and the closed door 226. Fluid lines (e.g., tubing) may be coupled to the cassette 202 in a known manner, such as via a connector, and may further include valves for controlling fluid flow to and from fluid bags including fresh dialysate and warming pouch. In some embodiments, when a cassette 202 is incorporated, at least a portion of the fluid lines (e.g., tubing) may be integral to the cassette 202. Prior to operation, a user may open the door 226 to insert a fresh cassette 202 and to remove the used cassette 202 after operation.

The cassette 202 may be placed in the cassette compartment 214 of the dialysis machine 200 for operation. The dialysis machine 200 may manage flowing dialysate into a patient's abdomen, and removal of the used dialysate and waste after a predetermined amount of time. During operation, dialysate fluid may be flowed into a patient's abdomen via the cassette 202, and spent dialysate, waste, and/or excess fluid may be removed from the patient's abdomen via the cassette 202.

While the dialysate is present in a peritoneal cavity of the patient, the dialysate may absorb contaminants and/or particulates from the patient's blood. PD uses the patient's peritoneum in the abdomen as a membrane across which fluids and dissolved substances (e.g., electrolytes, urea, glucose, albumin, osmotically active particles, and other small molecules) are exchanged from the blood. PD for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The dialysis machine 200 may operate the pumps (as will be described in greater detail below) to move the fluid. In use, the pumps apply force to the cassette 202, that connect a fluid reservoir, e.g., dialysate bags to a catheter at the patient's peritoneum. By operation of the pumps, fresh dialysate may be introduced into the patient's peritoneum. Likewise, the pumps may draw fluid from the patient's peritoneum into a fluid reservoir or drain to waste. Multiple dialysate bags may be used including a clean fluid reservoir and a waste fluid reservoir. Operation of the pumps in conjunction with valves controls delivery or retrieval of fluid.

In connection with PD machine 200, the heating element 152 may be in the form of a heater tray 240 including a heating element 235 positioned, for example, on top of the housing 242 of the dialysis machine 200. The heater tray 240 may be any size and shape to accommodate a bag of dialysate (e.g., a 5 L bag of dialysate) for batch heating. In use, for example as illustrated in the example embodiment of FIG. 3A, dialysate bags 234 may be suspended from hooks on the sides of a cart 244, and a heater bag 237 may be positioned in the heater tray 240. Connectors and tubing ports may connect the dialysate bags 234 and lines for transferring dialysate. Dialysate from the dialysate bags 234 may be transferred to the heater bag 237 in batches. For example, a batch of dialysate may be transferred from one or more dialysate bags 234 to the heater bag 237, where the dialysate is heated by the heating element 235. When the batch of dialysate has reached a predetermined temperature (e.g., approximately 98°–100° F., 37° C.), the batch of dialysate may be flowed into the patient. The dialysate bags 234 and the heater bag 237 may be connected to the cassette 202 via dialysate bag lines or tubing 238 and a heater bag line or tubing 238, respectively. The dialysate bag lines 238 may be used to pass dialysate from dialysate bags 234 to the cassette 202 during use, and a heater bag line 246 may be used to pass dialysate back and forth between the cassette 202 and the heater bag 237 during use. In addition, a patient line 248 and a drain line 250 may be connected to the cassette 202. The patient line 248 may be connected to a patient's abdomen via a catheter and may be used to pass dialysate back and forth between the cassette 202 and the patient's peritoneal cavity by the pumps during use. The drain line 250 may be connected to a drain or drain receptacle and may be used to pass dialysate from the cassette 202 to the drain or drain receptacle during use.

As previously mentioned, fluid may leak from the cassette 202. Specifically, fluid may leak at the interface between the cassette 202 and the pumps (e.g., pump heads) formed in the PD machine 200 (e.g., a leak can develop, for example, at the interface between a piston or pump head of a pump mechanism in the dialysis machine and a membrane proximate a fluid chamber formed in the cassette). In addition, and/or alternatively, the cassette 202 may be improperly positioned within the cassette compartment 214 of the PD machine 200.

Referring to FIG. 3B, a more detailed view of the cassette interface 210 of the dialysis machine 200 is shown. As shown, in one embodiment, the PD machine 200 includes pumps or pumping mechanisms, which include pistons 233A, 233B with pump heads 241A, 241B attached to piston shafts that can be axially moved within piston access ports 236A, 236B formed in the cassette interface 210. In one embodiment, the piston shafts are connected to stepper motors that can be operated to move the pistons 233A, 233B axially inward and outward such that the pump heads 241A, 241B move axially inward and outward within the piston access ports 236A, 236B. In one embodiment, the stepper motors drive lead screws, which move nuts inward and outward along the lead screws. The nuts, in turn, are connected to the pistons 233A, 233B and thus cause the pistons 233A, 233B to move inward and outward as the stepper motors rotate the lead screws. Stepper motor controllers provide the necessary current to be driven through the windings of the stepper motors to move the pistons 233A, 233B. The polarity of the current determines whether the pistons 233A, 233B are advanced or retracted.

The PD machine 200 may also include encoders (e.g., optical encoders) that measure the rotational movement of the lead screws. The axial positions of the pistons 233A, 233B can be determined based on the rotational movement of the lead screws, as determined by the encoders. Thus, the measurements of the encoders can be used to accurately position the pump heads 241A, 241B of the pistons 233A, 233B.

In use, when the cassette 202 is properly positioned within the cassette compartment 214 of the PD machine 200 with the door 226 closed, the pump heads 241A, 241B of the PD machine 200 align with pump chambers 239A, 239B of the cassette 202 such that the pump heads 241A, 241B can be mechanically connected to dome-shaped fastening members of the cassette 202 overlying the pump chambers 239A, 239B. As a result of this arrangement, movement of the pump heads 241A, 241B toward the cassette 202 during treatment can decrease the volume of the pump chambers 239A, 239B and force dialysate out of the pump chambers 239A, 239B, while retraction of the pump heads 241A, 241B away from the cassette 202 can increase the volume of the pump chambers 239A, 239B and cause dialysate to be drawn into the pump chambers 239A, 239B.

As shown in FIG. 3B, the cassette interface 210 may also include pressure sensors 251A, 251B that align with pressure sensing chambers 263A, 263B of the cassette 202 when the cassette 202 is positioned within the cassette compartment 214. When included, portions of a membrane of the cassette 202 that overlie the pressure sensing chambers 263A, 263B adhere to the pressure sensors 251A, 251B using vacuum pressure. Specifically, clearance around the pressure sensors 251A, 251B communicates vacuum to the portions of the cassette membrane overlying the pressure sensing chambers 263A, 263B to hold those portions of the cassette membrane tightly against the pressure sensors 251A, 251B. The pressure of fluid within the pressure sensing chambers 263A, 263B causes the portions of the cassette membrane overlying the pressure sensing chambers 263A, 263B to contact and apply pressure to the pressure sensors 251A, 251B. The pressure sensors 251A, 251B can be any sensors that are capable of sensing the fluid pressure in the sensing chambers 263A, 263B.

The PD machine 200 may also include inflatable members (not shown) positioned within inflatable member ports (not shown) in the cassette interface 210. The inflatable members align with depressible dome regions of the cassette 202 when the cassette 202 is positioned within the cassette compartment 214 of the PD machine 200. The inflatable members act as valves to direct dialysate through the cassette 202 in a desired manner during use. In particular, the inflatable members bulge outward beyond the surface of the cassette interface 210 and into contact with the depressible dome regions of the cassette 202 when inflated, and retract into the inflatable member ports and out of contact with the cassette 202 when deflated. By inflating certain inflatable members to depress their associated dome regions on the cassette 202, certain fluid flow paths within the cassette 202 can be occluded. Thus, dialysate can be pumped through the cassette 202 by actuating the pump heads 241A, 241B, and can be guided along desired flow paths within the cassette 202 by selectively inflating and deflating the various inflatable members.

The PD machine 200 may also include locating pins 249 (FIG. 4) extending from the cassette interface 210. When the door 226 is in the open position, the cassette 202 can be loaded onto the cassette interface 210 by positioning the top portion of the cassette 202 under the locating pins 249 and pushing the bottom portion of the cassette 202 toward the cassette interface 210. The cassette 202 is dimensioned to remain securely positioned between the locating pins 249 and a spring loaded latch extending from the cassette interface 210 to allow the door 226 to be closed over the cassette 202. The locating pins 249 help to ensure that proper alignment of the cassette 202 within the cassette compartment 214 is maintained during use.

As shown, the door 226 may include cylindrical recesses 252A, 252B that substantially align with the pistons 233A, 233B when the door 226 is in the closed position. When the cassette 202 is positioned within the cassette compartment 214, hollow projections (not shown) of the cassette 202, inner surfaces of which partially define the pump chambers 239A, 239B, fit within the recesses 252A, 252B. The door 226 may further include a pad that is inflated during use to compress the cassette 202 between the door 226 and the cassette interface 210. With the pad inflated, the portions of the door 226 forming the recesses 252A, 252B support the projections of the cassette 202 and the planar surface of the door 226 supports the other regions of the cassette 202. The door 226 can counteract the forces applied by the inflatable members and thus allows the inflatable members to actuate the depressible dome regions on the cassette 202. The engagement between the door 226 and the hollow projections of the cassette 202 can also help to hold the cassette 202 in a desired fixed position within the cassette compartment 214 to further ensure that the pistons 233A, 233B align with the fluid pump chambers 239A, 239B of the cassette 202.

In use, the controller is connected to the pressure sensors 251A, 251B, to the stepper motors (e.g., the drivers of the stepper motors) that drive the pistons 233A, 233B, and to the encoders that monitor rotation of the lead screws of the stepper motors such that the controller can receive signals from and transmit signals to those components of the system. In use, the controller monitors the components to which it is connected to determine whether any complications exists within the PD system 100. In the event of complications, the controller can trigger one or more alarms and initiates communication (e.g., wirelessly) to activate one or more of the peripheral devices. The peripheral devices can, for example, be activated in a manner to get the attention of the patient and/or to draw the attention of the patient to a region of the PD system 100 determined to be experiencing the complication. Additional information and details on the operation of the PD machine including the pumps is disclosed in United States Published Patent Application No. 2015/0025449, filed on Jul. 22, 2013, entitled Activating Peripheral Devices in a Dialysis System, the entire contents of which are incorporated by reference herein.

Figure 4:
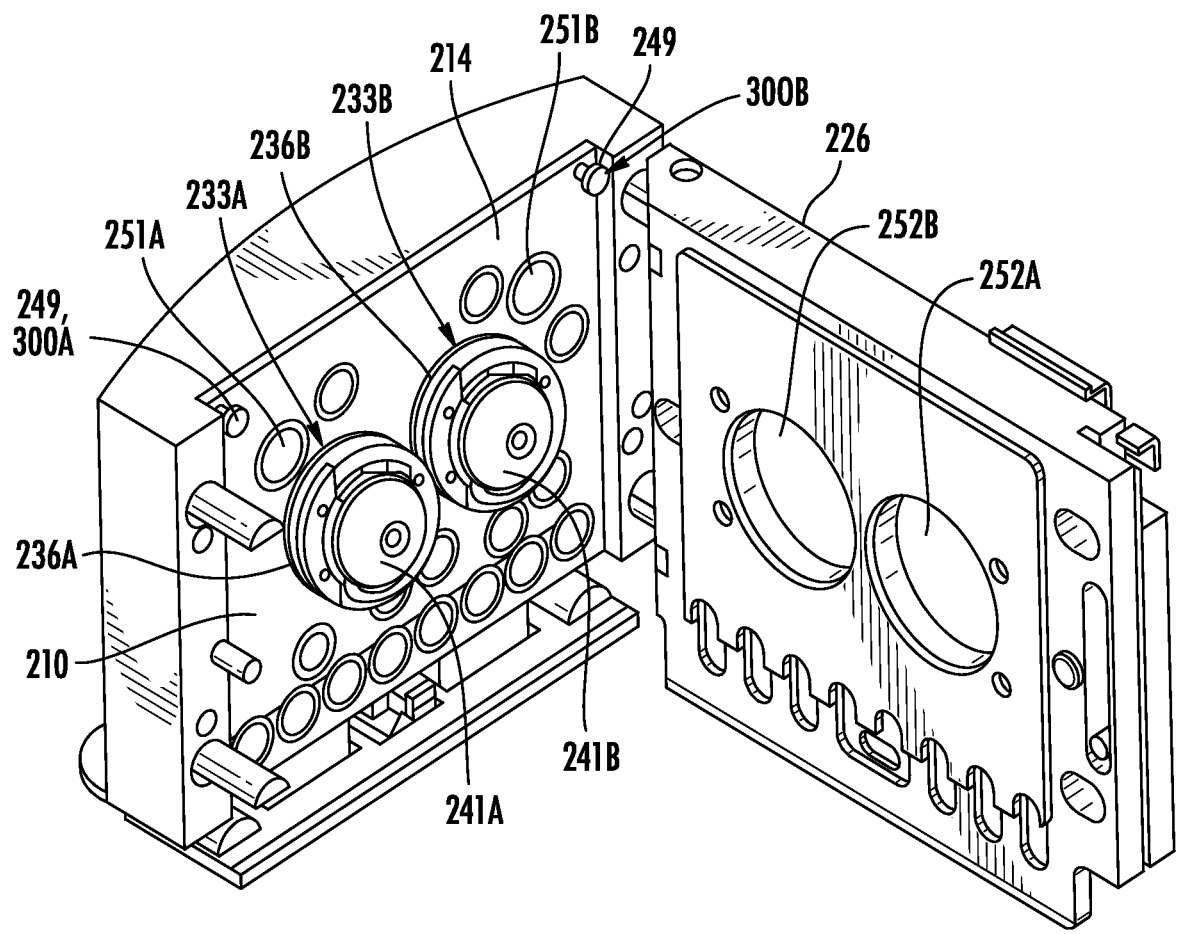
FIG. 4 illustrates a detailed view of an example of an embodiment of a cassette compartment including one or more sensors that may be used in connection with the dialysis machine of FIGS. 2, 3A, and 3B in accordance with one or more aspects of the present disclosure.

In accordance with one or more aspects of the present disclosure, the dialysis machine, such as PD machine 150, 200, includes one or more sensors associated with the cassette interface 210 to detect proper loading, insertion, positioning, alignment, etc. of the cassette 202 into the cassette compartment 214. Referring to FIG. 4, in accordance with one aspect of the present disclosure, the dialysis machine 200 may include one or more sensors 300 to detect proper loading of the cassette 202 within the PD machine 200. For example, the PD machine 200 may include one or more sensors 300 associated with the cassette interface 210 in the PD machine 200. The one or more sensors 300 being arranged and configured to detect proper loading of the cassette 202 within the cassette compartment 214 of the PD machine 200. The one or more sensors 300 may be any suitable sensor now known or hereafter developed to detect proper loading of the cassette 202 within the cassette compartment 214 of the PD machine 200. In use, the one or more sensors 300 may be arranged and configured to transmit an input, a signal, etc. to, for example, a controller (e.g., controller 155), which upon receiving the input or signal that the cassette 202 is not properly positioned transmits an alarm and/or prevents the dialysis machine 200 from starting a treatment cycle. For example, the controller may prevent the pump heads 241A, 241B from extending if the cassette 202 is misaligned within the PD machine 200 (e.g., actuation of the dialysis machine 200 is prevented if proper alignment of the cassette 202 within the dialysis machine 200 is not detected). In addition, and/or alternatively, the dialysis machine 200 can issue an alarm, an alert, etc. (e.g., a visual alert such as, for example, a flashing LED, an audio alert, etc.) to indicate that the cassette 202 is not properly aligned within the cassette interface 214 of the dialysis machine 200 so that the patient or care giver can take appropriate corrective measures.

For example, in one embodiment and as illustrated in FIG. 4, the one or more sensors 300 may be a limit switch (e.g., a mechanical limit switch). The limit switch may extend, protrude, or the like from the surface of the cassette interface 210. For example, as illustrated, the PD machine 200 may include first and second limit switches 300A, 300B built into the first and second locating pins 249 located on the surface of the PD machine 200. In use, proper positioning of the cassette 202 within the cassette compartment 214 of the PD machine 200 will cause the cassette 202 to contact the limit switches 300A, 300B. Contacting the limit switches 300A, 300B will cause the limit switches to transition from a first stage or configuration to a second stage or configuration indicating that the cassette 202 is properly positioned.

Alternatively, as previously mentioned, the one or more sensors 300 may take on other forms. For example, the one or more sensors may be in the form of optical sensors. In use, the one or more optical sensors may be arranged and configured to detect the location of the various edges (e.g., perimeter) of the cassette 202 within the cassette compartment 214 of the dialysis machine 200 to detect proper alignment of the cassette 202 within the cassette compartment 214 of the dialysis machine 200. Alternatively, and/or in addition, the cassette 202 may include one or more registration marks printed on an outer surface of the cassette 202. In use, the dialysis machine 200 may include one or more image sensors. In use, the image sensors can be arranged and configured to determine alignment of the cassette 202 based on imaging of the registration marks on the cassette 202. Alternatively, the one or more sensors may be in the form of one or more capacitive sensors arranged and configured to detect proper positioning of the cassette 202 within the cassette compartment 214. For example, in one embodiment, the one or more capacitive sensors may be arranged and configured to detect whether the cassette 202 is properly seated within the cassette compartment 214 such as, for example, the capacitive sensors may be arranged and configured to detect if the cassette 202 is sitting flush with the surface of the cassette compartment 214 indicating that the cassette 202 is properly positioned within the cassette compartment 214 of the dialysis machine 200. It should be appreciated that any combination of sensors may be utilized to detect proper positioning, alignment, etc. of the cassette 202 within the cassette compartment 214.

Figure 5:
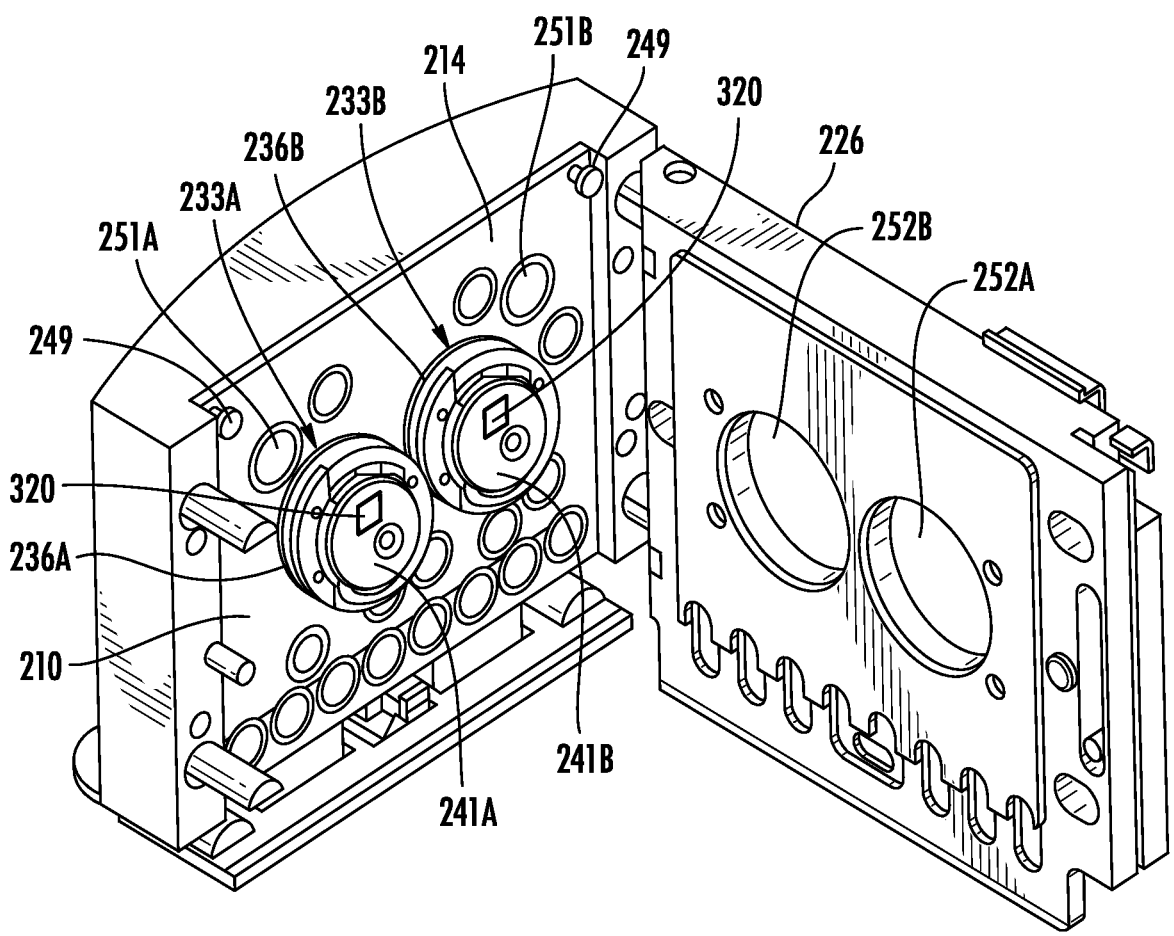
FIG. 5 illustrates a detailed view of an alternate example of an embodiment of a cassette compartment including one or more sensors that may be used in connection with the dialysis machine of FIGS. 2, 3A, and 3B in accordance with one or more aspects of the present disclosure.

In addition, and/or alternatively, referring to FIG. 5, in accordance with one or more aspects of the present disclosure, the dialysis machine 200 may include one or more sensors 320 to detect a leak within the PD machine 200. In use, the one or more sensors for detecting a leak within the PD machine 200 may be used in combination with the one or more sensors to detect proper loading, insertion, positioning, alignment, etc. of the cassette 202 into the cassette compartment 214, or separately therefrom. For example, the PD machine 200 may include one or more sensors 320 associated with the pumps or pistons 233A, 233B in the PD machine 200. In one embodiment, as shown in FIG. 5, the pump heads 241A, 241B may include one or more capacitive sensors 320 arranged and configured to detect a presence of a liquid on the surface of the pump heads 241A, 241B or on the surface of the cassette interface surrounding the pump heads 241A, 241B. In addition, and/or alternatively, the surface of the cassette 202 may include one or more capacitive sensors arranged and configured to detect a presence of a liquid on the surface of the pump heads 241A, 241B or on the surface of the cassette interface surrounding the pump heads 241A, 241B. During use, if a leak is detected (e.g., if the capacitive sensor 320 detects liquid on the surface of the pump heads 241A, 241B or on the surface of the cassette 202), a signal can be transmitted by the capacitive sensors 320 to the controller resulting in an alarm and/or stopping the dialysis treatment. Additional information on this embodiment can be found in U.S. patent application Ser. No. 16/680,778, filed on Nov. 12, 2019, entitled "Piston Assembly Including Leak Detection in a Dialysis Machine", the entire contents of which are hereby incorporated by reference in its entirety.

In addition, and/or alternatively, in accordance with one or more aspects of the present disclosure, the dialysis machine, such as PD machine 150, 200, includes one or more sensors associated with the cassette interface to detect proper operation of the pumps (e.g., pistons) of the dialysis machine 200. In use, the one or more sensors for detecting proper operation of the pumps (e.g., pistons) may be used in combination with the one or more sensors to detect proper loading, insertion, positioning, alignment, etc. of the cassette 202 into the cassette compartment 214, with the one or more sensors to detect a leak within the PD machine, or separately therefrom. That is, for example, the PD machine 200 may include one or more sensors arranged and configured to aid with detecting proper operation of the pumps (e.g., pistons). In one embodiment, in addition to the encoders used to detect a position of the pump heads 241A, 241B via, for example, indirect measurements of the rotation of the lead screw (as previously described), the dialysis machine 200 may include one or more additional sensors positioned in the dialysis machine adjacent to, for example, the pump heads 241A, 241B to monitor proper operation of the pumps (e.g., pistons).

In use, the one or more sensors are arranged and configured to detect proper operation of the pumps (e.g., pistons) within the PD machine. For example, as previously mentioned, during manufacturing of the dialysis machines, problems may arise such as, for example, using parts that are bent, etc. that may cause the pump heads 241A, 241B to be misaligned in the dialysis machine. As a result, engagement of the pump heads 241A, 241B in the dialysis machine 200 with the pump chambers 239A, 239B of the cassette 202 positioned within the dialysis machine 200 may be inaccurate, which may cause problems resulting in leaks in the cassette 202 or prevent proper positioning, alignment, etc. of the pump heads 241A, 241B with the pump chambers 239A, 239B, respectively, of the cassette 202.

The one or more sensors may be any suitable sensor now known or hereafter developed to detect proper operation of the pumps (e.g., pistons) within the PD machine 200. In use, the one or more sensors may be arranged and configured to transmit an input, a signal, etc. to, for example, a controller (e.g., controller 155), which upon receiving the input or signal that the pumps (e.g., pistons) are not properly operating, transmits an alarm and/or prevents the dialysis machine 200 from starting a treatment cycle. For example, the controller prevents the pump heads 241A, 241B from extending if the pistons are determined to be improperly operating (e.g., prevents actuation of the dialysis machine if proper operation of the pistons within the dialysis machine is not detected). In addition, and/or alternatively, the dialysis machine can issue an alarm, an alert, etc. (e.g., a visual alert such as, for example, a flashing LED, an audio alert, etc.) to indicate that the pumps (e.g., pistons) are not properly operating so that the patient or care giver can take appropriate corrective measures.

Figure 6:
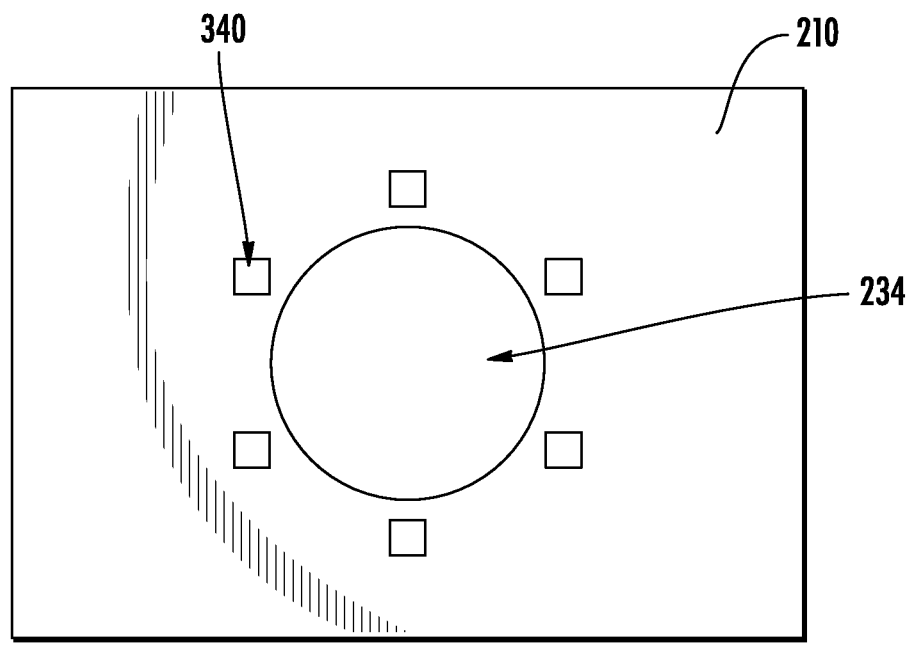
FIG. 6 illustrates a view of an example of an embodiment of a cassette compartment including one or more sensors that may be used in connection with the dialysis machine of FIGS. 2, 3A, and 3B in accordance with one or more aspects of the present disclosure.

For example, in one example of an embodiment, referring to FIG. 6, one or more sensors 340 can be positioned about the pumps (e.g., pistons). In use, the sensors 340, which may be in the form of proximity sensors, are arranged and configured to monitor axial alignment of the pump assemblies. For example, as illustrated, in one embodiment, a plurality of proximity sensors 340 (e.g. such as, for example, six to eight proximity sensors) may be positioned radially around an axis of travel of the pumps (e.g., pistons). Thereafter, in use, as the pumps (e.g., pistons) move, the proximity sensors 340 can detect alignment of the pumps (e.g., pistons). For example, the proximity sensors 340 can detect misalignment based on the relative signal strength of the different proximity sensors. A detected misalignment may cause a signal to be transmitted to the controller, which may cause an alarm and/or stopping treatment cycle thus indicating to the patient and/or care giver that the dialysis machine may need to be serviced to repair or replace the pump assembly. In use, the plurality of proximity sensors 340 may also detect proper operation of the pumps (e.g., pistons) such that the sensors 340 can detect if the pump heads 241A, 241B are actually being extended or retracted. For example, if the pump heads 241A, 241B are removed from the pump assembly and/or the lead screw threads are stripped, the pump heads 241A, 241B may not move with rotation of the lead screw. This can be detected by the proximity sensors.

Thus arranged, during normal operation of the dialysis machine 150, 200, fluid (e.g., dialysate) is properly contained within its respective fluid bags and/or fluid lines. The sensors 300, 320, 340 may be configured to monitor the dialysis machine to ensure proper operation and/or patient safety. In the event that the sensor detects misalignment of the cassette 202 within the cassette compartment 214, detects fluid on the outer surface of the cassette 202 or pumps, and/or detects improper operation of the pumps, the dialysis machine 150, 200 may be configured to react to the detection in any number of ways, including initiating alarms and/or causing one or more operational conditions. For example, once a condition has been detected, a signal may be sent from the sensor 300, 320, 340 to, for example, the controller of the dialysis machine to: activate an alarm, halt operations, or a combination thereof. For example, the dialysis machine 150, 200 may be arranged and configured to generate an alarm condition, such as a visual and/or audible notifier. For example, a signal may be sent to the user interface portion of the dialysis machine to indicate the condition, and/or an audio or a light indicator may be triggered. In some embodiments, the dialysis machine 150, 200 may transmit (e.g., via a wireless connection) the alarm condition to a remote location, including but not limited to a doctor's office, hospital, call center, and technical support. For example, the dialysis machine 150, 200 may provide real time remote monitoring of machine operation. The dialysis machine 150, 200 may include a memory for storing data, or may transmit data to a local or remote server at scheduled intervals. In addition, and/or alternatively, the dialysis machine 150, 200 may be arranged and configured to automatically shut off operation, or allow the user to monitor, pause, and/or cease the dialysis operation based on the detection. In this manner, the dialysis treatment can be halted and/or the condition corrected.

Figure 7:
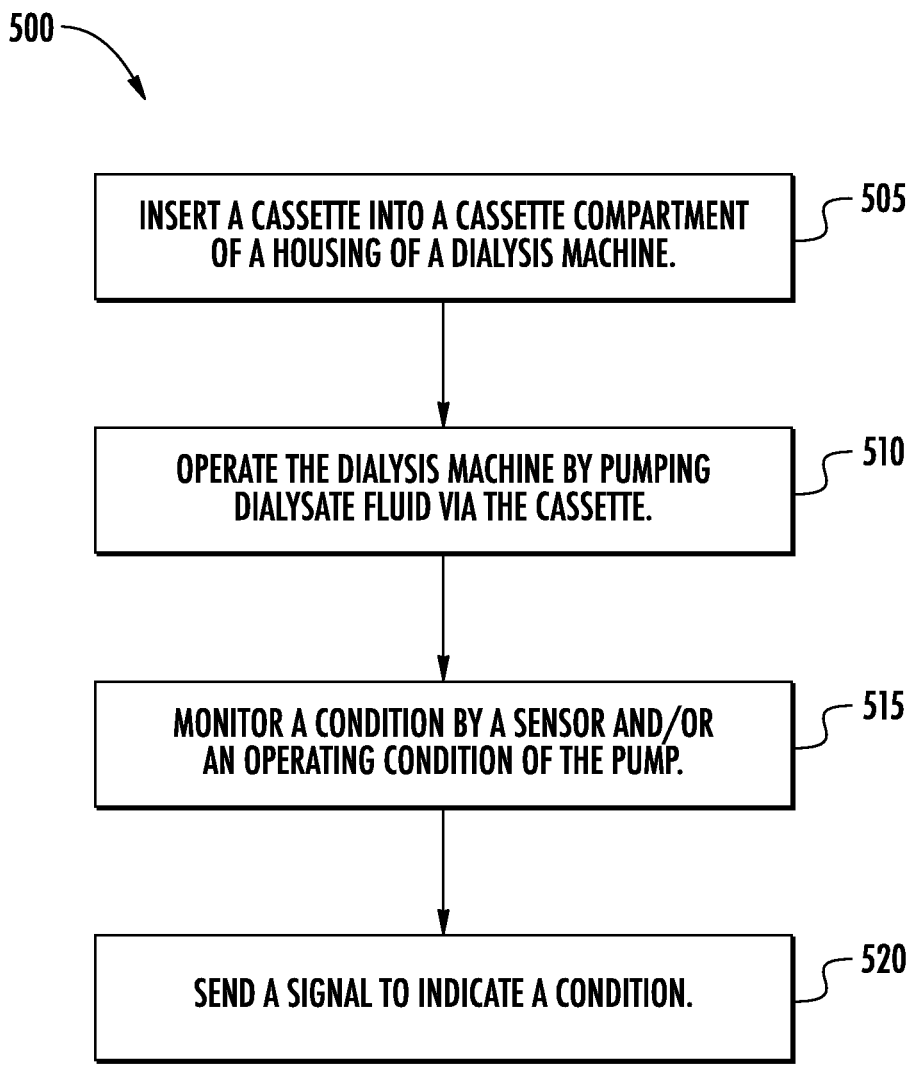
FIG. 7 illustrates a flow diagram of an example of a method of detecting a monitored condition in a dialysis machine according to one or more embodiments of the present disclosure.

Referring to FIG. 7, a flow diagram 500 of a method of detecting improper alignment of the cassette within the cassette compartment, a leak during a dialysis operation, and/or improper operation of the pumps (e.g., pistons) according to one or more embodiments of the present disclosure is shown. At step 505, components of the dialysis machine 150, 200 are inserted, for example, a cassette 202 may inserted into a cassette compartment of a housing of the dialysis machine. At step 510, the dialysis machine is operated by pumping dialysate fluid via the cassette. As described above, in a peritoneal dialysis operation, fresh dialysate may be pumped into an abdomen of a patient, and spent dialysate, including waste and excess fluid, may flow out of the patient's abdomen. At step 515, a condition of the dialysis machine such as, for example, alignment of the cassette within the cassette compartment, a leak during a dialysis operation, and/or improper operation of the pumps (e.g., pistons) is monitored by one or more sensors 300, 320, 340. At step 520, when a condition is detected in the dialysis machine, a signal is transmitted from the sensor to the processor of the machine. As described above, the machine may send an audible or a visual indication of the condition, and alternatively, or additionally, automatically stop dialysis operation.

The system described herein has been explained in connection dialysis machines having a particular configuration. It is contemplated that the system described herein may be used with dialysis machines having other configurations, for example, different types of dialysis machines and/or dialysis machines having cassettes positionable in other configurations and having other features. The system described herein may be used with any appropriate dialysis machine and/or other medical devices utilizing disposable cassettes that would benefit from leak detection.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

While the systems and techniques described herein for detecting leaks have been largely explained with reference to a dialysis machine, in particular, a peritoneal dialysis machine, the systems and techniques described for detecting leaks may be used in connection with other types of medical treatment systems and/or machines, such as a hemodialysis machine or other medical treatment device involving medical fluids. In some implementations, the dialysis machine may be configured for use in a patient's home (e.g., a home dialysis machine). The home dialysis machine can take the form of a peritoneal dialysis machine or a home hemodialysis machine.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:
1. A dialysis system, comprising:
 a dialysis machine for transferring dialysate to a patient from a dialysate source, the dialysis machine including a housing including a cassette compartment, a pump positioned within the housing, and one or more sensors; and
 a cassette positionable within the cassette compartment, the cassette being in fluid communication with the patient and the dialysate source;

wherein, when the cassette is positioned within the cassette compartment, movement of the pump causes the dialysate to be transferred from the dialysate source to the patient;

wherein the one or more sensors are arranged and configured to detect proper alignment of the cassette within the cassette compartment; and wherein the dialysis machine further comprises a plurality of capacitive sensors, at least one of which is directly positioned on a pump head of a piston of the pump, each of the plurality of capacitive sensors arranged and configured to detect a presence of a liquid on a surface of the pump head of the piston.

2. The dialysis system of claim 1, wherein the one or more sensors is one or more limit switches, the one or more limit switches arranged and configured so that the proper alignment of the cassette within the cassette compartment causes the cassette to trigger the one or more limit switches.

3. The dialysis system of claim 2, wherein the dialysis machine includes one or more locating pins extending from a surface thereof, the one or more limit switches built into the one or more locating pins.

4. The dialysis system of claim 1, wherein the one or more sensors includes an optical sensor arranged and configured to detect a location of the cassette within the cassette compartment.

5. The dialysis system of claim 4, wherein the optical sensor is arranged and configured to detect a location of a perimeter of the cassette relative to the cassette compartment to detect the proper alignment of the cassette within the cassette compartment.

6. The dialysis system of claim 1, wherein the cassette includes one or more registration marks printed on an outer surface thereof, the one or more sensors includes an image sensor arranged and configured to detect alignment of the cassette relative to the cassette compartment based on imaging of the one or more registration marks on the cassette.

7. The dialysis system of claim 1, wherein the one or more sensors includes one or more second capacitive sensors arranged and configured to detect the proper alignment of the cassette within the cassette compartment.

8. The dialysis system of claim 7, wherein the one or more second capacitive sensors are arranged and configured to detect if the cassette is properly seated within the cassette compartment via determining if the cassette is positioned adjacent with a surface of the cassette compartment.

9. The dialysis system of claim 1, wherein at least one of the one or more sensors are arranged and configured to detect proper axial extension of the pump.

10. The dialysis system of claim 9, wherein the at least one of the one or more sensors arranged and configured to detect the proper axial extension of the pump includes a plurality of proximity sensors positioned about the pump.

11. The dialysis system of claim 10, wherein the plurality of proximity sensors are arranged and configured to detect alignment of the pump during extension.

12. The dialysis system of claim 1, wherein the one or more sensors are configured to send a signal based on a detection of improper alignment of the cassette within the cassette compartment; and
wherein the signal is sent to a user interface of the dialysis machine, an audible indicator, or a light indicator, or a combination thereof.

13. The dialysis system of claim 12, wherein the dialysis machine is arranged and configured to automatically terminate the transferring of the dialysate to the patient from the dialysate source upon receipt of the signal.

14. A dialysis system, comprising:
a dialysis machine for transferring dialysate to a patient from a dialysate source, the dialysis machine including a housing including a cassette compartment, a pump positioned within the housing, and one or more sensors;
a cassette positionable within the cassette compartment, the cassette being in fluid communication with the patient and the dialysate source; and
one or more locating pins extending from a cassette interface of the cassette compartment, the one or more locating pins configured to ensure proper alignment of the cassette within the cassette compartment;
wherein, when the cassette is positioned within the cassette compartment, movement of the pump causes the dialysate to be transferred from the dialysate source to the patient;
wherein the one or more sensors are arranged and configured to: detect the proper alignment of the cassette within the cassette compartment, detect proper axial alignment of the pump, or a combination thereof,
wherein the dialysis machine further comprises a plurality of capacitive sensors, at least one of which is directly positioned on a pump head of a piston of the pump, each of the plurality of capacitive sensors arranged and configured to detect a presence of liquid on a surface of the pump head of the piston, and
wherein at least one of the one or more sensors comprises a limit switch built into the one or more locating pins, the limit switch configured so that the proper alignment of the cassette within the cassette compartment causes the cassette to contact the limit switch.

15. The dialysis system of claim 14, wherein contact of the cassette with the limit switch causes the limit switch to transition from a first configuration to a second configuration indicating that the cassette is properly positioned.

16. The dialysis system of claim 14, wherein the one or more sensors includes an optical sensor arranged and configured to detect a location of the cassette within the cassette compartment.

17. The dialysis system of claim 16, wherein the optical sensor is arranged and configured to detect a location of a perimeter of the cassette relative to the cassette compartment to detect the proper alignment of the cassette within the cassette compartment.

18. The dialysis system of claim 14, wherein the cassette includes one or more registration marks printed on an outer surface thereof, the one or more sensors includes an image sensor arranged and configured to detect alignment of the cassette relative to the cassette compartment based on imaging of the one or more registration marks on the cassette.

19. The dialysis system of claim 14, wherein the one or more sensors includes one or more second capacitive sensors arranged and configured to detect the proper alignment of the cassette within the cassette compartment.

20. The dialysis system of claim 19, wherein the one or more second capacitive sensors are arranged and configured to detect if the cassette is properly seated within the cassette compartment via determining if the cassette is positioned adjacent with a surface of the cassette compartment.

21. The dialysis system of claim 14, wherein at least one of the one or more sensors are arranged and configured to detect proper axial extension of the pump.

22. The dialysis system of claim 21, wherein the at least one of the one or more sensors arranged and configured to detect the proper axial extension of the pump includes a plurality of proximity sensors positioned about the pump.

23. The dialysis system of claim 22, wherein the plurality of proximity sensors are arranged and configured to detect alignment of the pump during extension.

24. The dialysis system of claim 14, wherein the one or more sensors are configured to send a signal based on a detection of improper alignment of the cassette within the cassette compartment; and wherein the signal is sent to a user interface of the dialysis machine, an audible indicator, or a light indicator, or a combination thereof.

25. The dialysis system of claim 24, wherein the dialysis machine is arranged and configured to automatically terminate the transferring of the dialysate to the patient from the dialysate source upon receipt of the signal.

\* \* \* \* \*